United States Patent
Ito et al.

(10) Patent No.: US 10,071,219 B1
(45) Date of Patent: Sep. 11, 2018

(54) ANESTHETIC TANK, AND SYSTEM FOR PREVENTING ERRONEOUS ANESTHETIC INJECTION

(71) Applicant: ACOMA MEDICAL INDUSTRY CO., LTD., Bunkyo-ku, Tokyo (JP)

(72) Inventors: Masaki Ito, Tokyo (JP); Hideki Uchida, Tokyo (JP); Kei Shimada, Tokyo (JP); Yuji Shirai, Tokyo (JP); Koji Fujii, Tokyo (JP)

(73) Assignee: ACOMA MEDICAL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 15/491,675

(22) Filed: Apr. 19, 2017

(30) Foreign Application Priority Data

Feb. 28, 2017 (JP) ................................. 2017-036338

(51) Int. Cl.
*B65D 79/02* (2006.01)
*A61M 16/18* (2006.01)

(52) U.S. Cl.
CPC ... *A61M 16/183* (2013.01); *A61M 2205/6045* (2013.01)

(58) Field of Classification Search
CPC .. B65D 5/4212; B65D 79/02; B65D 2203/00; B65D 2203/12; B65D 2203/04
USPC ........................................ 206/459.1; 141/351
See application file for complete search history.

(56) References Cited

U.S. PATENT DOCUMENTS

| | | | |
|---|---|---|---|
| 6,539,988 B1 * | 4/2003 | Cowan | B60H 1/00585 137/614.04 |
| 6,929,041 B2 | 8/2005 | Falligant et al. | |
| 7,287,561 B2 | 10/2007 | Turker et al. | |
| 2008/0308179 A1 | 12/2008 | Danielsen | |

FOREIGN PATENT DOCUMENTS

DE 102005037924 B3 3/2007

* cited by examiner

*Primary Examiner* — King M Chu
(74) *Attorney, Agent, or Firm* — Arent Fox LLP

(57) ABSTRACT

An anesthetic tank includes an insertion mouth for inserting an injection adapter of an anesthetic container, and a storage portion communicating with the insertion mouth. A volatile anesthetic inside of the anesthetic container is injected into the storage portion. An identifying member is arranged on the outside of the insertion mouth and is rotatable around the center axis of the insertion mouth. The identifying member has key groove formed in the internal surface of an insertion hole for inserting the injection adapter. The key groove are used for identifying the type of the volatile anesthetic in collaboration with keys formed in the injection adapter. A cover member has an opening formed in the position facing the insertion mouth and the insertion hole and presses the peripheral part of the identifying member.

9 Claims, 12 Drawing Sheets

(A)

(B)

(C)

FIG. 10
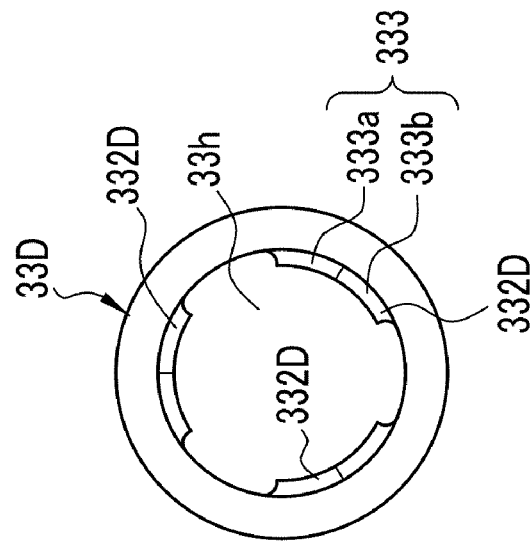
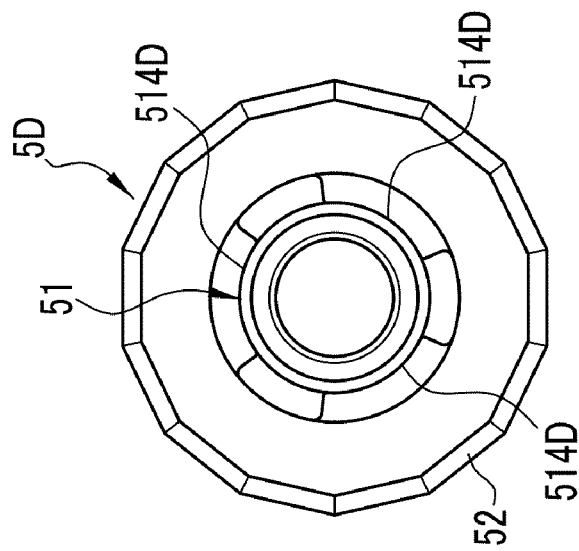

ANESTHETIC TANK, AND SYSTEM FOR PREVENTING ERRONEOUS ANESTHETIC INJECTION

CROSS-REFERENCE TO RELATED APPLICATIONS

This application claims priority to Japanese Patent Application No. 2017-036338, filed Feb. 28, 2017. The disclosure of the priority document application is incorporated in its entirety herein by reference.

TECHNICAL FIELD

The present invention relates to an anesthetic tank which is injected with a liquid volatile anesthetic, and a system for preventing an erroneous anesthetic injection which is capable of preventing an unsuitable volatile anesthetic from being injected in error into the anesthetic tank.

BACKGROUND ART

An anesthesia system anesthetizing a patient includes: an anesthetic vaporizer vaporizing a volatile anesthetic and regulating the concentration of the vaporized anesthetic gas; and an anesthetic tank supplying the anesthetic vaporizer with an anesthetic. The anesthetic tank is arranged inside of the anesthetic vaporizer, or alternatively, is separated from the anesthetic vaporizer and connected via piping to the anesthetic vaporizer. The thus-configured anesthetic tank includes an anesthetic injection portion for injecting a volatile anesthetic from an anesthetic container having a bottle shape. The anesthetic injection portion is provided with a substantially cylindrical insertion mouth communicating with the anesthetic tank. On the other hand, the anesthetic container is provided with a mouth portion, and on the periphery of the mouth portion, a mouth thread is formed and used for setting an injection adapter. The injection adapter is provided with a substantially cylindrical insertion portion inserted into the insertion mouth of the anesthetic injection portion. The injection adapter is inserted into the anesthetic injection portion, so that the volatile anesthetic can be injected from the anesthetic container through the injection adapter and the anesthetic injection portion into the anesthetic tank.

There are several types of anesthetics such as sevoflurane, isoflurane, enflurane and halothane, and the individual types of anesthetics differ in the properties such as the boiling point, the saturated vapor pressure and the MAC (minimum alveolar concentration). In order to realize the concentration of a volatile anesthetic with precision, an exclusive anesthetic vaporizer is needed for each type of volatile anesthetic (e.g., refer to Non-Patent Document 1). Hence, a medical facility manages to prevent a specified type of volatile anesthetic from being injected into an anesthetic tank different from the exclusive one. For the purpose of ensuring this management, systems for preventing an erroneous anesthetic injection were invented which determine an injection adapter and an anesthetic vaporizer for every type of volatile anesthetic and thereby prevent the injection of a volatile anesthetic unsuitable for an anesthetic vaporizer (e.g., refer to Patent Documents 1 to 4).

Patent Document 1 provides a system for preventing an erroneous anesthetic injection which includes: a set of keys formed in an insertion portion of an injection adapter thereof, the set of keys indicating the type of a volatile anesthetic by the widths of the keys and the arrangement intervals between the keys; and a set of key groove formed in an insertion mouth of an anesthetic injection portion thereof, the set of key groove having the widths and the arrangement intervals fit for the set of keys of the injection adapter. Therefore, if the keys of the insertion portion engage with the key groove of the insertion mouth, then the insertion portion is inserted into the insertion mouth, thereby preventing an erroneous injection of the volatile anesthetic.

Patent Document 2 provides a system for preventing an erroneous anesthetic injection which includes: a polygonal key formed in the peripheral surface of an insertion portion of an injection adapter thereof, the key indicating the type of a volatile anesthetic by the number of the angles, and a set of key groove formed in the front end of the insertion portion, the set of key groove being shaped like the teeth of a comb and the key groove being equal in number to the angles of the polygonal key; and a polygonal keyhole formed in an insertion mouth of an anesthetic injection portion thereof, the polygonal keyhole being fit for the polygonal key of the injection adapter, and a set of keys formed in the insertion mouth, the set of keys being shaped like the teeth of a comb and being fit for the set of key groove shaped like the teeth of a comb. Therefore, if the polygonal key and the comb-teeth key groove of the insertion portion engage with the polygonal keyhole and the comb-teeth keys of the insertion mouth respectively, then the insertion portion is inserted into the insertion mouth, thereby preventing an erroneous injection of the volatile anesthetic.

Patent Document 3 provides a system for preventing an erroneous anesthetic injection which includes: a cylindrical member formed in an insertion portion of an injection adapter thereof, the cylindrical member being rotatable around the center axis of the insertion portion and being formed in the peripheral surface thereof with a set of keys indicating the type of a volatile anesthetic by the number of the keys and the arrangement intervals between the keys; and a set of key groove formed in an insertion mouth of an anesthetic injection portion thereof, the set of key groove being fit for the set of keys of the injection adapter. Therefore, if the keys of the insertion portion engage with the key groove of the insertion mouth, then the insertion portion is inserted into the insertion mouth, thereby preventing an erroneous injection of the volatile anesthetic.

Patent Document 4 provides a system for preventing an erroneous anesthetic injection which includes an injection adapter and an anesthetic injection portion the configurations of which are similar to those of Patent Document 2. The injection adapter has an insertion portion formed with a polygonal key and a set of key groove shaped like the teeth of a comb, the insertion portion being rotatable around the insertion axis thereof with respect to the injection adapter. The anesthetic injection portion has an insertion mouth formed with a polygonal keyhole and a set of keys shaped like the teeth of a comb, the insertion mouth being arranged inside of a cylindrical stub (filler connection stub). The stub is rotatable around the insertion axis thereof with respect to the anesthetic injection portion. In the connection region between the injection adapter and the anesthetic injection portion, an insertion assistant portion is provided, the insertion assistant portion being used for positioning (centering) the polygonal key and the polygonal keyhole so that the former is fitted into the latter.

In the systems for preventing an erroneous anesthetic injection according to Patent Documents 1 and 2, a person needs to insert the injection adapter into the anesthetic injection portion while checking the positions of the keys and the key groove through visual or touching inspection.

This would complicate the injection work. Besides, when the keys of the injection adapter engage with the key groove of the anesthetic injection portion, the anesthetic container may be rotated to loosen the attachment of the injection adapter, thereby causing the anesthetic container to leak the volatile anesthetic.

In the system for preventing an erroneous anesthetic injection according to Patent Document 3, the cylindrical member of the injection adapter is rotated and thereby leads the keys to engage with the key groove. Therefore, the attachment of the injection adapter cannot be loosened, thereby hindering the anesthetic container from leaking the volatile anesthetic. However, the small cylindrical member located at the front end of the injection adapter needs rotating so that the keys and the key groove engage each other. Accordingly, it is impossible to simplify the injection work.

In contrast, in the system for preventing an erroneous anesthetic injection according to Patent Document 4, upon inserting the insertion portion of the injection adapter into the insertion mouth of the anesthetic injection portion, the insertion assistant portion rotates the insertion mouth and the stub so that the polygonal key of the former is fitted into the polygonal keyhole of the latter. Therefore, the key can be easily fitted into the keyhole, thereby avoiding loosening the attachment of the injection adapter and hence preventing the anesthetic container from leaking the volatile anesthetic.

PRIOR ART DOCUMENTS

Patent Documents

[Patent Document 1] U.S. Pat. No. 6,929,041
[Patent Document 2] U.S. Pat. No. 7,287,561
[Patent Document 3] U.S. Patent Laid-Open No. 2008/0308179
[Patent Document 4] German Patent Application Laid-Open No. 102005037924 specification Non-Patent Document

[Non-Patent Document 1] "Special Issue: Present situation and progress of devices for general anesthesia, and vaporizers" written by Tomohiro Michino and Shuji Dohi in Iryou kikigaku (The Japanese journal of medical instrumentation) Vol. 75 (2005) No. 8 edited and published by Japanese Society of Medical Instrumentation

SUMMARY OF THE INVENTION

Problems to be Solved by the Invention

However, in the injection adapter and the anesthetic injection portion of Patent Document 4, the insertion portion and the stub conventionally united therewith respectively are each formed as a separate component element in a rotatable manner. Accordingly, the injection adapter and the anesthetic injection portion have a complicated structure and hence may break down more likely, thereby lowering the safety. Besides, seal parts such as an O-ring are employed for preventing a leak of the volatile anesthetic from the insertion portion and the stub. Since those seal parts have low durability, they may be degraded to cause a leak of the volatile anesthetic. If the rotation parts are securely joined together with high precision, then a leak of the volatile anesthetic can be prevented without seal parts. However, this requires highly-precise machining, which would raise the prices of the injection adapter, and an anesthetic vaporizer, an anesthetic tank or the like provided with the anesthetic injection portion, as compared with the conventional prices.

In addition, an anesthetic vaporizer and an anesthetic tank need producing for each type of volatile anesthetic, and desirably, as many common component parts as possible should be employed for them and the component parts should be easily exchanged in accordance with the types of volatile anesthetics. However, in the anesthetic injection portion of Patent Document 4, the whole stub needs exchanging in accordance with each type of volatile anesthetic, and the stub needs sealing so that an anesthetic can be prevented from leaking while the stub is rotating. Consequently, the anesthetic injection portion could not be regarded as an easily-exchangeable component part.

In order to solve the above problems, it is an object of the present invention to provide an anesthetic tank and a system for preventing an erroneous anesthetic injection which are capable of: preventing a leak of a volatile anesthetic without taking measures to prevent the leak by seal parts or the like even if the attachment of an injection adapter is loosened; and simplifying component parts to be exchanged in accordance with a plurality of types of anesthetic tanks.

Means for Solving the Problems

In order to solve the above problems, an anesthetic tank according to the above which includes an insertion mouth for inserting an injection adapter attached to a mouth portion of an anesthetic container and a storage portion communicating with the insertion mouth, the storage portion being injected from the injection adapter inserted into the insertion mouth with a volatile anesthetic inside of the anesthetic container, comprises: an identifying member which: has a disk shape; is arranged on the outside of the insertion mouth and rotatable around the center axis of the insertion mouth; has an insertion hole formed in the position facing the insertion mouth, the insertion hole being used for inserting the injection adapter; and has a first identification portion formed in the internal surface of the insertion hole, the first identification portion being used for identifying the type of the volatile anesthetic to be injected in collaboration with a second identification portion formed in the injection adapter; and a cover member which has an opening formed in the position facing the insertion mouth and the insertion hole, the opening being used for inserting the injection adapter, and presses the peripheral part of the identifying member from above the identifying member, the identifying member accepting the injection adapter by rotating up to the position where the first identification portion engages with the second identification portion if the injection adapter having the second identification portion fit for the first identification portion is inserted into the insertion hole and thereby the second identification portion presses the first identification portion, and hindering insertion of the injection adapter by leading the first identification portion to block the space necessary for the insertion of the second identification portion if the injection adapter having the second identification portion unfit for the first identification portion is inserted into the insertion hole.

According to the above, in the anesthetic tank of claim 1, wherein as the anesthetic tank, a plurality of types are employed in accordance with types of the volatile anesthetic, and the plurality of types of anesthetic tanks are mutually different only in the identifying member.

A system for preventing an erroneous anesthetic injection according to the above includes an injection adapter attached to a mouth portion of an anesthetic container and the anesthetic tank according to the above, wherein the injection adapter includes the second identification portion formed in the peripheral surface of an insertion portion of the injection adapter inserted into the insertion mouth, the second identification portion being used for identifying the type of the volatile anesthetic to be injected into the anesthetic tank in collaboration with the first identification portion.

According to the above, the insertion portion of the injection adapter is inserted into the insertion mouth of the anesthetic tank, and thereby, the identifying member arranged on the outside of the insertion mouth and rotatable around the center axis of the insertion mouth comes into contact with the insertion portion of the injection adapter. If the injection adapter having the second identification portion fit for the first identification portion is inserted into the insertion hole and thereby the second identification portion presses the first identification portion, then the identifying member accepts the injection adapter by rotating up to the position where the first identification portion engages with the second identification portion. On the other hand, if the injection adapter having the second identification portion unfit for the first identification portion is inserted into the insertion hole, then the identifying member hinders insertion of the injection adapter by leading the first identification portion to block the space necessary for the insertion of the second identification portion.

According to the above, in the system for preventing an erroneous anesthetic injection of the above, either the first identification portion or the second identification portion is a set of keys which indicates the type of the volatile anesthetic by at least any one of the widths, the positions and the number of the keys, and the other is a set of key groove which is fit for the set of keys.

According to the above, in the system for preventing an erroneous anesthetic injection of the above, each of the keys is formed at the end with a first inclined plane for rotating the identifying member in a first direction around the center axis of the insertion mouth and a second inclined plane for rotating the identifying member in a second direction opposite to the first direction.

According to the above, in the system for preventing an erroneous anesthetic injection of the above, a plurality of the keys and a plurality of the key groove are arranged at regular intervals around the center axis of the insertion portion or the insertion mouth respectively.

Advantages of the Invention

According to the above, the insertion portion of the injection adapter is inserted into the insertion mouth, and thereby, the identifying member arranged on the outside of the insertion mouth and rotatable around the center axis of the insertion mouth comes into contact with the insertion portion of the injection adapter. Then, the second identification portion of the insertion portion presses the first identification portion and rotates the identifying member. As a result, the insertion portion can be inserted into the insertion mouth without rotating the anesthetic container. This avoids loosening the attachment of the injection adapter and thereby prevents a leak of a volatile anesthetic. Besides, the injection adapter can be inserted into the insertion mouth of the anesthetic tank without positioning the second identification portion of the insertion portion and the first identification portion of the insertion mouth so that the former engages with the latter. Therefore, the injection work of the volatile anesthetic becomes simpler.

In addition, the identifying member is arranged on the outside of the insertion mouth, and hence, the volatile anesthetic does not leak from the identifying member. This dispenses with: seal parts such as an O-ring; highly-precise machining necessary for preventing a leak of the volatile anesthetic; and the like. Furthermore, the identifying member is arranged on the outside of the insertion mouth and is only pressed by the cover member, so that the identifying member can be easily exchanged. Therefore, as described in claim 2, even if the plurality of types of anesthetic tanks are employed in accordance with the types of volatile anesthetics, then the individual anesthetic tanks can be utilized simply by exchanging the identifying members alone. This makes it possible to produce the plurality of types of anesthetic tanks at an extremely-low cost and with ease.

According to the above, either the first identification portion or the second identification portion is a set of keys and the other is a set of key groove. Therefore, a choice can be optionally made as to which of the two members should be formed with a set of keys or a set of key groove in accordance with various conditions such as the shapes of the insertion portion and the insertion mouth. This heightens the degree of freedom in design for the injection adapter and the anesthetic tank, thereby facilitating the injection work in the system for preventing an erroneous anesthetic injection.

According to the above, the first inclined plane for rotating the identifying member in the first direction and the second inclined plane for rotating the identifying member in the second direction are provided, and thereby, the required rotational angle of the identifying member narrows as compared with the case where the identifying member is rotated along an inclined plane in only one direction. The narrower-angle rotation of the identifying member enables the first identification portion and the second identification portion to be positioned in a short period of time so that the former engages with the latter. Therefore, the injection work of the volatile anesthetic becomes quicker.

According to the above, the plurality of keys and the plurality of key groove are arranged at regular intervals around the center axis of the insertion portion or the insertion mouth respectively. Therefore, even if the second identification portion of the injection adapter is inserted at any position into the insertion mouth of the anesthetic tank, the identifying member performs the positioning quickly.

BRIEF DESCRIPTION OF THE DRAWINGS

FIG. 10 is a plan view of an injection adapter and an identifying member according to a second embodiment of the present invention.

MODE FOR CARRYING OUT THE INVENTION

First Embodiment

A first embodiment of the present invention will be below described with reference to the drawings.

Figure 1:
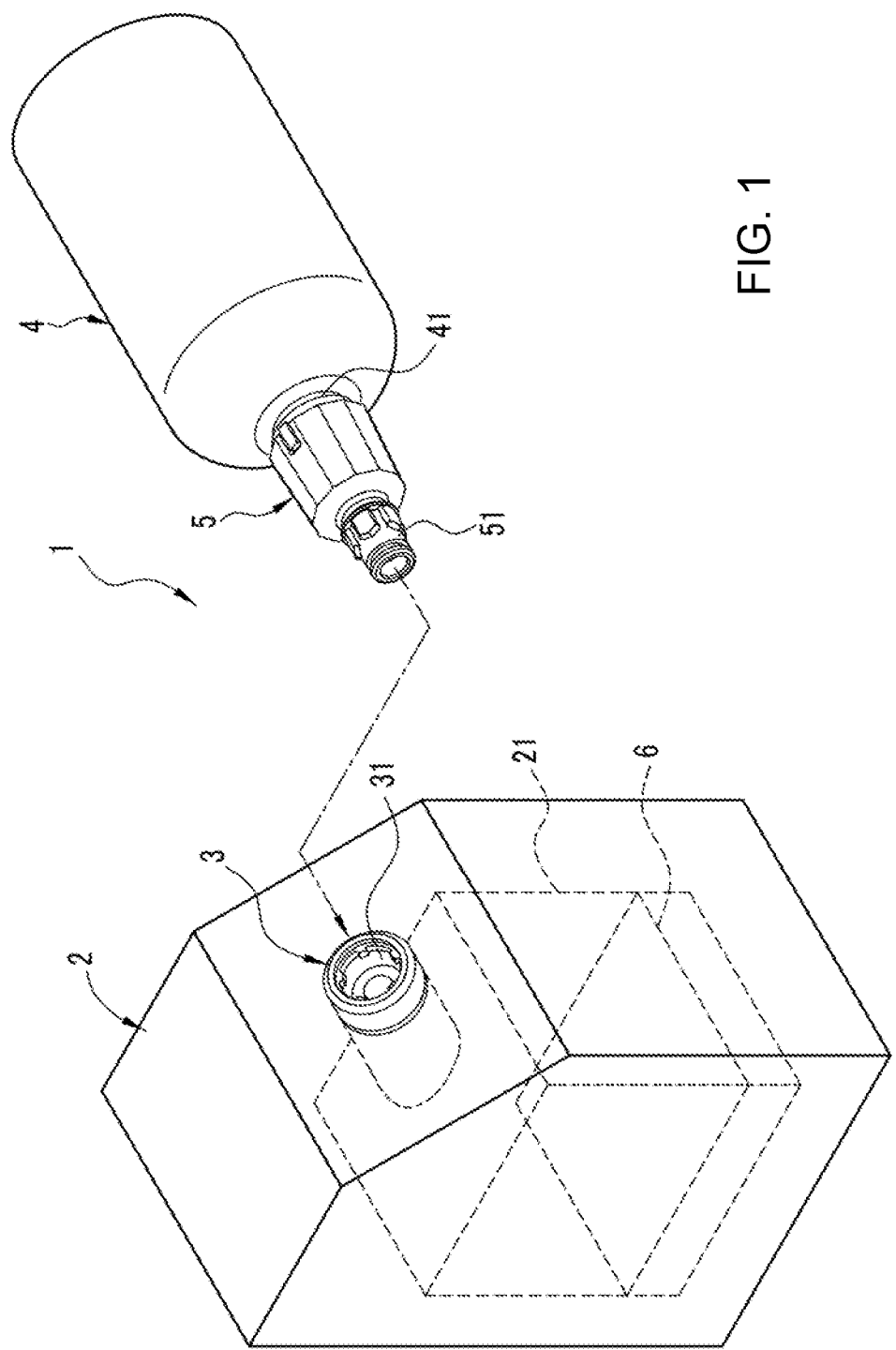
FIG. 1 is a perspective view of a system for preventing an erroneous anesthetic injection according to a first embodiment of the present invention.

FIG. 1 is a perspective view of a system 1 for preventing an erroneous anesthetic injection according to this embodiment. The system 1 for preventing an erroneous anesthetic injection is formed by an anesthetic tank 2 provided in an anesthetic vaporizer (not shown) and an injection adapter 5 attached to a mouth portion 41 of an anesthetic container 4. The anesthetic vaporizer vaporizes a volatile anesthetic 6 stored in a storage portion 21 and regulates the concentration of the vaporized anesthetic gas. The anesthetic vaporizer is arranged inside of an anesthesia system anesthetizing a patient. In short, this embodiment relates to the anesthetic tank 2 arranged inside of the anesthetic vaporizer.

The anesthetic tank 2 is provided with a circular insertion mouth 31 communicating with the storage portion 21. The insertion mouth 31 is formed in an erroneous-injection prevention portion 3 for preventing an erroneous injection of an anesthetic, or specifically, preventing an injection of the volatile anesthetic 6 unsuitable for the anesthetic tank 2. The erroneous-injection prevention portion 3 has the shape of a substantial cylinder and protrudes partly from the external surface of the anesthetic tank 2. The anesthetic container 4 has a mouth thread 411 (see FIG. 4) formed on the periphery of the mouth portion 41, and the injection adapter 5 is attached to the mouth thread 411. The injection adapter 5 is formed with a substantially cylindrical insertion portion 51 inserted into the insertion mouth 31 of the anesthetic tank 2. The insertion portion 51 is inserted into the insertion mouth 31, and then, the volatile anesthetic 6 stored in the anesthetic container 4 is injected from the anesthetic container 4 through the insertion mouth 31 into the storage portion 21.

Figure 2:
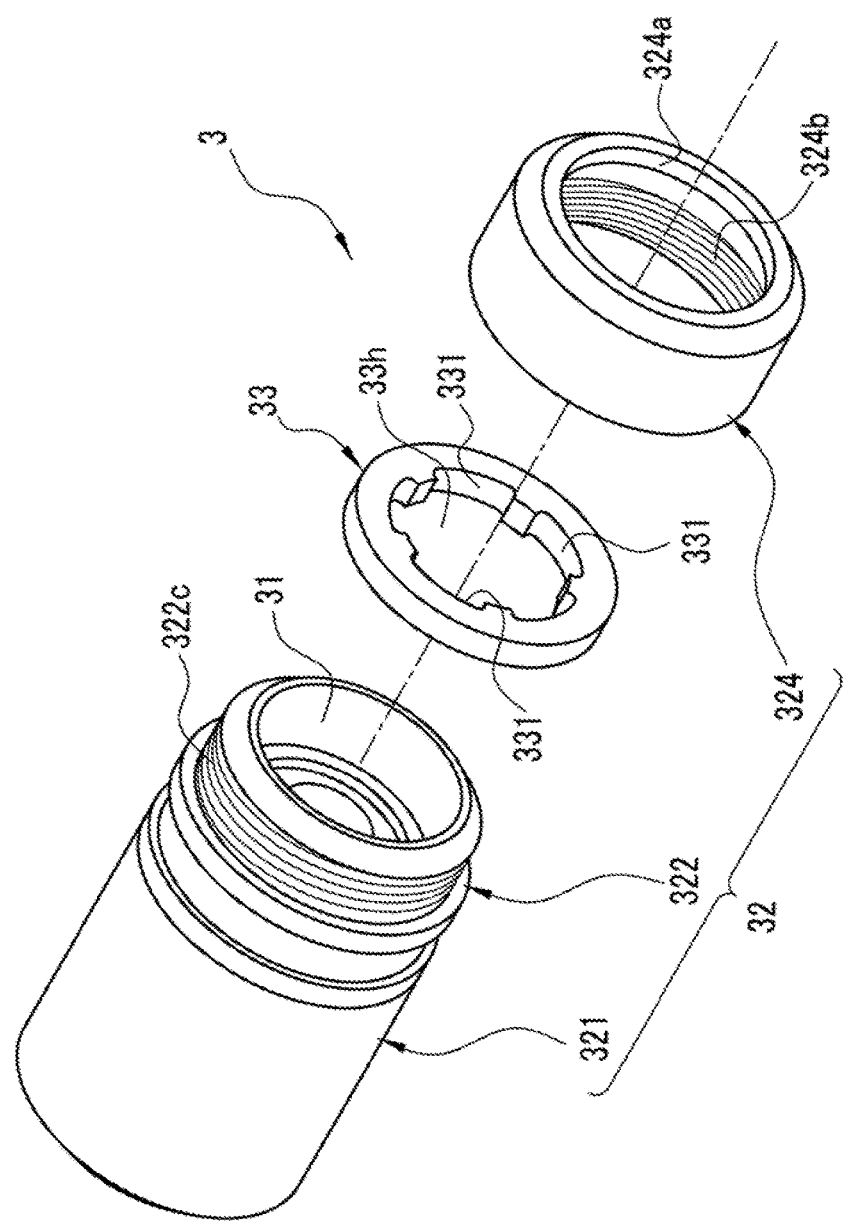
FIG. 2 is a perspective view showing the external shape of an erroneous-injection prevention portion of FIG. 1.
Figure 3:
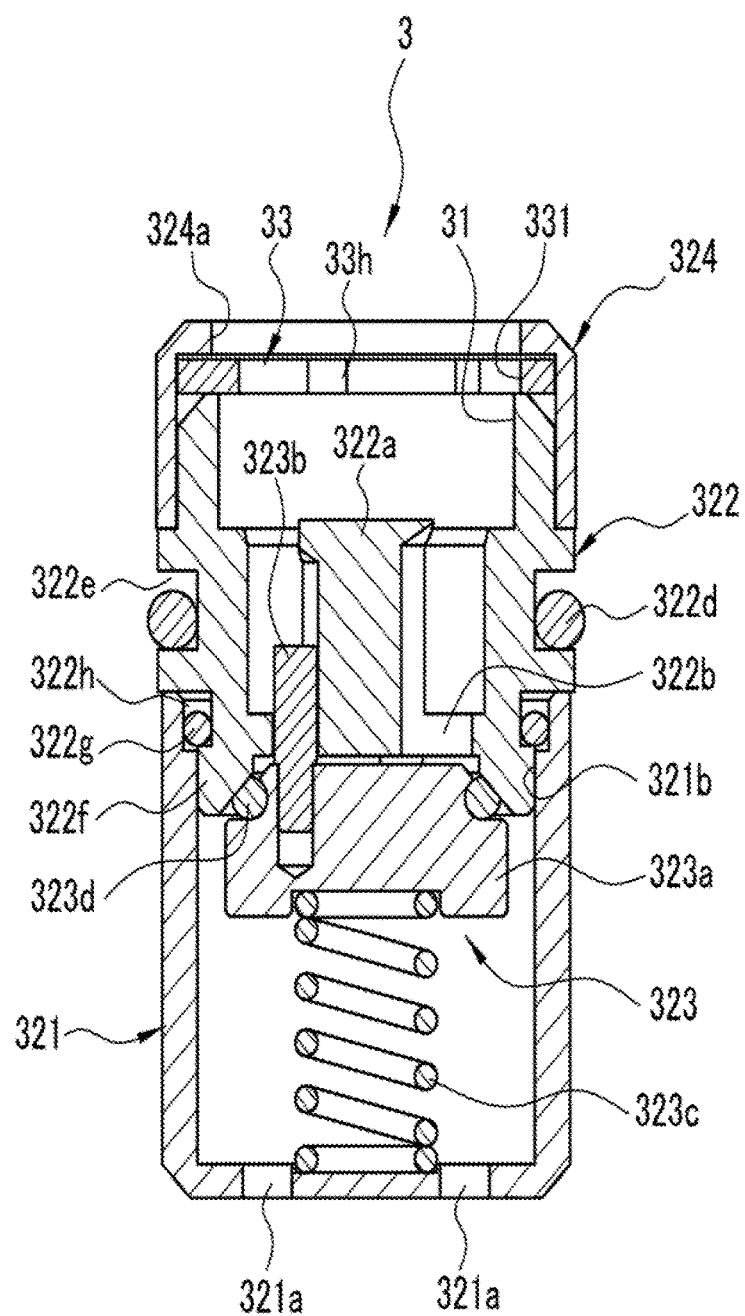
FIG. 3 is a sectional view showing a configuration of the erroneous-injection prevention portion of FIG. 1.

FIG. 2 is a perspective view showing the external shape of the erroneous-injection prevention portion 3 formed with the insertion mouth 31. FIG. 3 is a sectional view showing a configuration of the erroneous-injection prevention portion 3. The erroneous-injection prevention portion 3 includes a substantially cylindrical body portion 32 formed with the insertion mouth 31, and an identifying member 33 housed in the body portion 32.

The body portion 32 includes: a cylindrical pipe member 321; an intermediate member 322 fitted into the pipe member 321; a valve mechanism 323 arranged between the pipe member 321 and the intermediate member 322; a cover member 324 screwed onto the front end of the intermediate member 322.

The pipe member 321 has: a plurality of holes 321a formed in the bottom part, the volatile anesthetic 6 flowing through the holes 321a into the storage portion 21; and an opening portion 321b formed in the top part, the intermediate member 322 being fitted into the opening portion 321b. The pipe member 321 is arranged, together with the intermediate member 322, inside of the anesthetic tank 2.

The intermediate member 322 has the shape of a substantial cylinder and is formed on the inside with the insertion mouth 31. The insertion mouth 31 is formed on the inside with: an opening protrusion 322a for opening a valve mechanism 54 (see FIG. 6) of the injection adapter 5; and a plurality of holes 322b for leading the volatile anesthetic 6 to flow into the pipe member 321. The intermediate member 322 has: an external thread 322c formed on the periphery, the cover member 324 being fitted onto the external thread 322c; and a groove portion 322e, an O-ring 322d being fitted into the groove portion 322e and sealing the part between the intermediate member 322 and the anesthetic tank 2. The intermediate member 322 has a fitting portion 322f formed in the lower part, and the fitting portion 322f is fitted into the opening portion 321b of the pipe member 321. The fitting portion 322f has a groove portion 322h formed on the periphery, and an O-ring 322g is fitted into the groove portion 322h and seals the part between the fitting portion 322f and the pipe member 321.

The valve mechanism 323 includes: a valve body 323a; a pin 323b standing on the upper side of the valve body 323a; a spring 323c pressing the valve body 323a against the intermediate member 322; and an O-ring 323d sealing the part between the valve mechanism 323 and the internal-circumference surface of the fitting portion 322f. The valve body 323a has the shape of a substantial disk and has the edge of the upper surface chamfered so as to fit with the internal-circumference surface of the fitting portion 322f, and the O-ring 323d is fitted into there. The pin 323b has the shape of a substantial pillar, penetrates through the bottom surface of the intermediate member 322 and protrudes into the insertion mouth 31.

The cover member 324 has the shape of a substantial cylinder and has an opening portion (opening) 324a formed in the upper surface for opening the insertion mouth 31. The cover member 324 has an internal thread 324b formed in the internal-circumference surface, and the internal thread 324b is screwed onto the external thread 322c of the intermediate member 322.

The identifying member 33 has a disk shape and is arranged on the outside of the insertion mouth 31 and rotatable around the center axis of the insertion mouth 31. In the position facing the insertion mouth 31, the identifying member 33 is formed with an insertion hole 33h for inserting the insertion portion 51 of the injection adapter 5. The identifying member 33 has key groove (first identification portion) 331 formed in the internal surface of the insertion hole 33h, and the key groove 331 are used for identifying the type of the volatile anesthetic 6 to be injected in collaboration with keys (second identification portion) formed in the injection adapter 5. In summary, the identifying member 33: has the shape of a substantial ring; is housed in the space between the intermediate member 322 and the cover member 324; is held on the body portion 32 so as to be rotatable around the center axis of the insertion mouth 31; and has the key groove 331 identifying the type of the volatile anesthetic 6 suitable for the anesthetic tank 2. The identifying member 33 shown in the figures corresponds to, for example, sevoflurane, and the five key groove 331 are arranged at regular intervals in the circumferential directions. The identifying member 33 is made of, for example, a nonmetal such as a plastic which is useful for lightening the identifying member 33, rotating it smoothly, preventing it from damaging the injection adapter 5, and the like.

Figure 4:
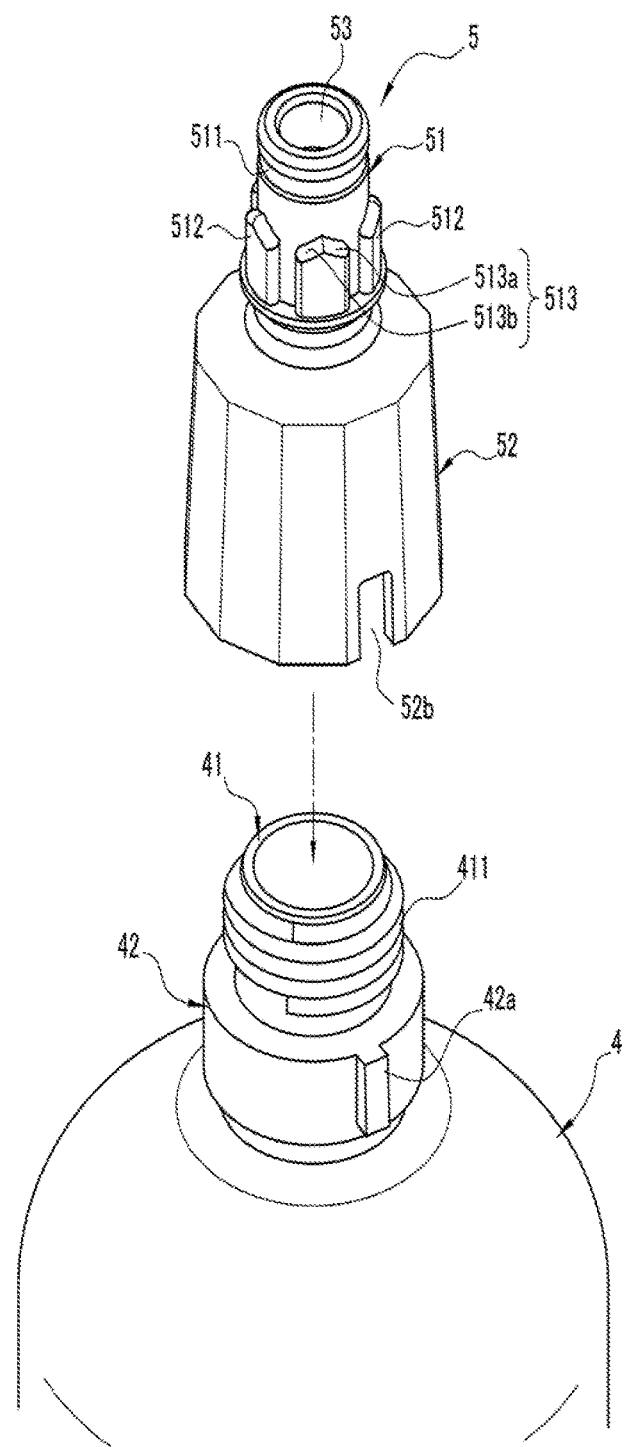
FIG. 4 is a perspective view showing the external shape of an injection adapter of FIG. 1.
Figure 5:
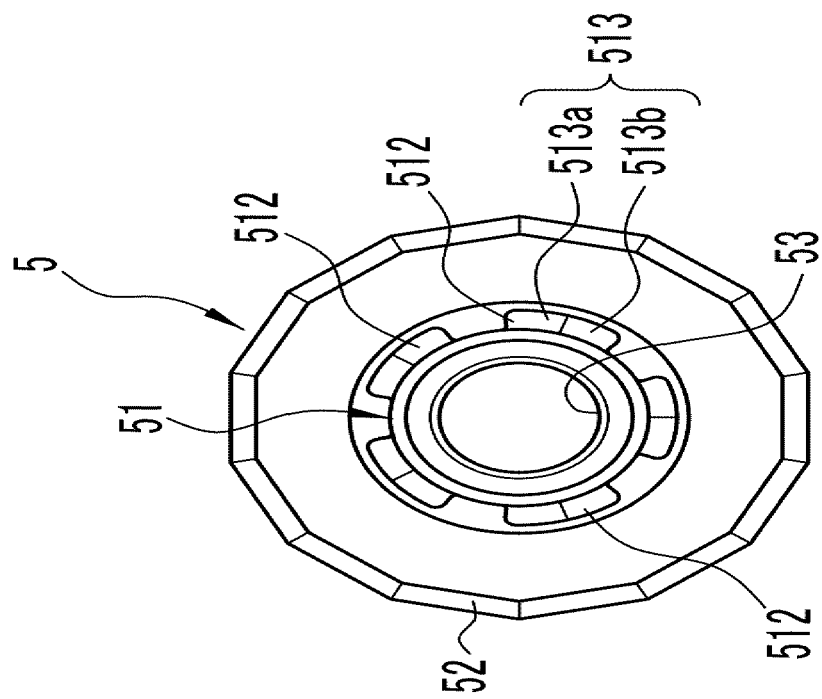
FIG. 5 is a plan view of the injection adapter of FIG. 1.
Figure 6:
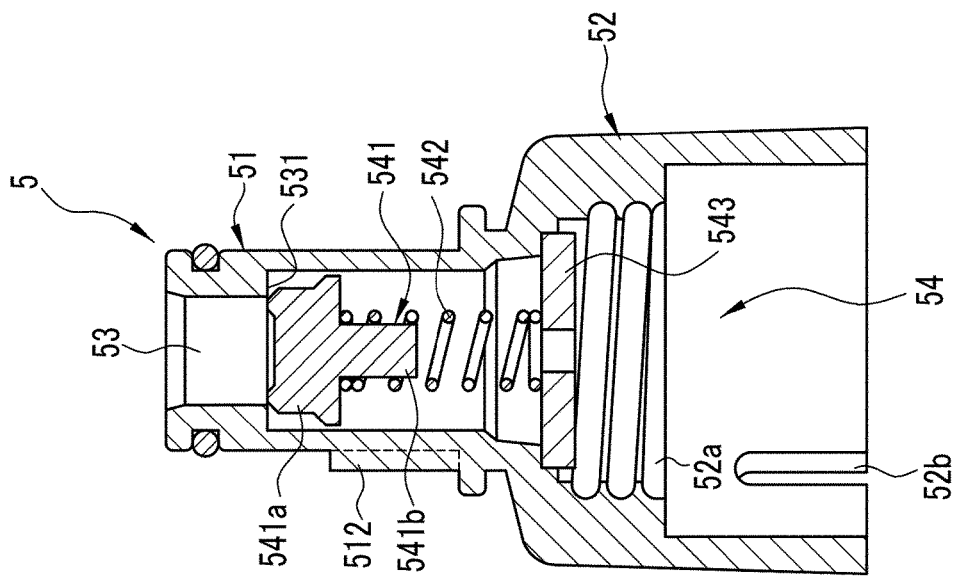
FIG. 6 is a sectional view showing a configuration of the injection adapter of FIG. 1.

FIG. 4 is a perspective view showing the external shape of the injection adapter 5, FIG. 5 is a plan view of the injection adapter 5, and FIG. 6 is a sectional view showing a configuration of the injection adapter 5. The injection adapter 5 includes: a substantially cylindrical base portion 52 having an internal thread 52a which is formed in the inner-diameter part and is screwed onto the mouth portion 41; and the insertion portion 51 arranged above the base portion 52. The base portion 52 has a notch 52b formed in the lower-end part which indicates the type of the volatile anesthetic 6 corresponding to the injection adapter 5 by the width and the arrangement interval of the notch 52b. The anesthetic container 4 is provided with a ringed collar 42 attached to the periphery of the mouth portion 41. The collar 42 is formed with a protrusion 42a, and the protrusion 42a has the width corresponding to the notch 52b of the injection adapter 5 and is arranged at the arrangement interval corresponding thereto. The notch 52b is fitted onto the protrusion 42a of the collar 42, and thereby, the injection adapter 5 is attached to the anesthetic container 4. This prevents the attachment of the injection adapter 5 to the anesthetic container 4 storing the volatile anesthetic 6 of any unsuitable type.

The insertion portion 51 has an O-ring 511 attached to a front-end part thereof, if the insertion portion 51 is inserted into the insertion mouth 31, then the O-ring 511 seals the part between the insertion portion 51 and the insertion mouth 31. The insertion portion 51 has a plurality of keys (second identification portion) 512 formed on the periphery of a base part thereof, and the keys 512 indicate the volatile anesthetic 6 of the suitable type. The injection adapter 5 shown in the figures corresponds to, for example, sevoflurane, and the five keys 512 are arranged at regular intervals in the circumferential directions. The keys 512 are each formed at the end with an inclined plane 513, and if the insertion portion 51 is inserted into the insertion mouth 31, then the inclined plane 513 comes into contact with the key groove 331 and thereby rotates the identifying member 33. In FIG. 4, the inclined plane 513 is formed by: a first inclined plane 513a for rotating the identifying member 33 in the counterclockwise direction (first direction); and a second inclined plane 513b for rotating the identifying member 33 in the clockwise direction (second direction). The first inclined plane 513a and the second inclined plane 513b are continuously arranged to shape the end part of the key 512 into a substantial mountain.

The identifying member 33 accepts the insertion portion 51 into the insertion mouth 31 if the shape of the key groove 331 is fit for the shape of the keys 512 of the insertion portion 51. On the other hand, the identifying member 33 hinders insertion of the insertion portion 51 into the insertion mouth 31 if the shape of the key groove 331 is unfit for the shape of the keys 512 of the insertion portion 51.

The insertion portion 51 and the base portion 52 are formed inside with a passage 53 for the volatile anesthetic 6. The passage 53 is formed inside with the valve mechanism 54 opening and closing the passage 53. The valve mechanism 54 is formed by a valve body 541, a spring 542 and a spring receiving member 543. The valve body 541 is formed by a disk portion 541a coming in contact with a stepped portion 531 inside of the passage 53, and a guide rod 541b located under the disk portion 541a. The valve body 541 is inserted through the passage 53. The spring 542 is arranged on the periphery of the guide rod 541b and presses the valve body 541 against the stepped portion 531. The spring receiving member 543 is fixed on the inside of the base portion 52, receives the lower end of the spring 542 and guides the guide rod 541b.

Figure 7:
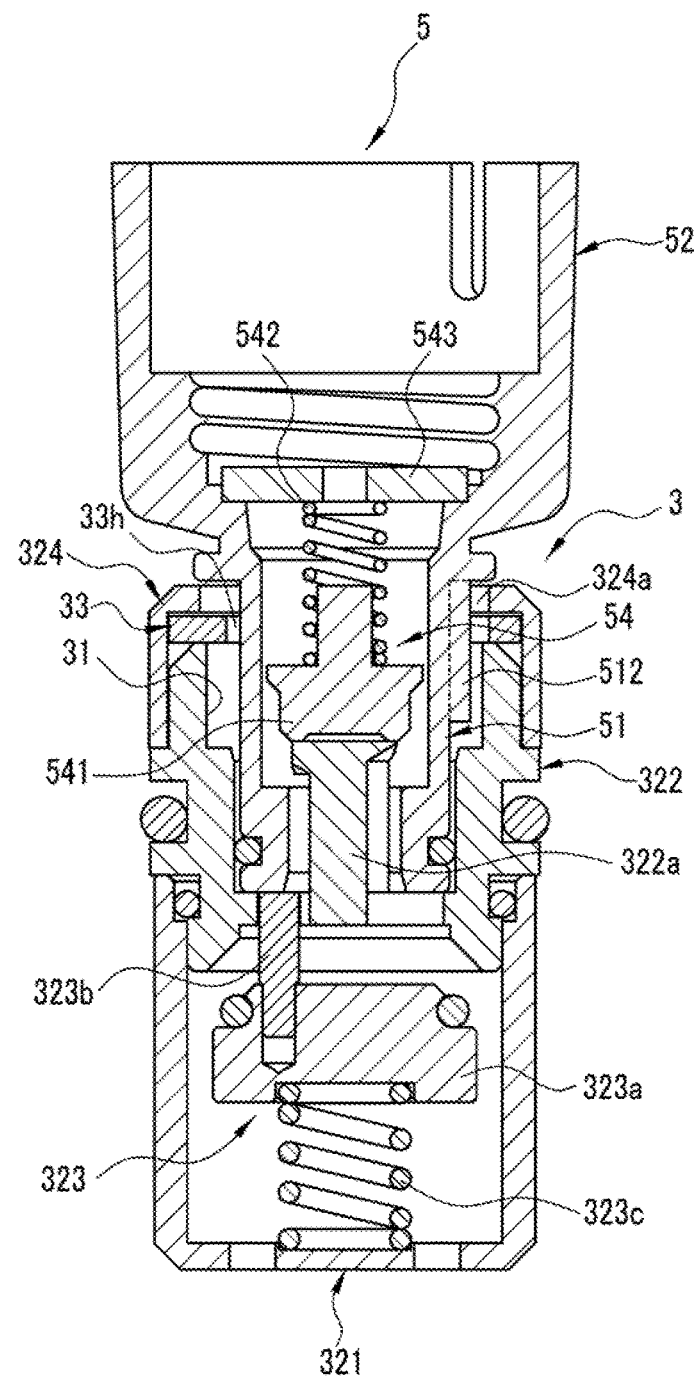
FIG. 7 is a sectional view showing an insertion portion of the injection adapter being inserted into an insertion mouth of an erroneous-injection prevention portion of FIG. 1.

Ordinarily, the valve mechanism 323 closes the insertion mouth 31 because the spring 323c applies force to the valve body 323a and the force causes the valve body 323a to come in close contact with the intermediate member 322. Similarly, the valve mechanism 54 ordinarily closes the passage 53 because the spring 542 applies force to the valve body 541 and the force causes the valve body 541 to come in close contact with the stepped portion 531. As shown in FIG. 7, if the insertion portion 51 of the injection adapter 5 is inserted into the insertion mouth 31 and presses the pin 323b, then the valve body 323a moves in the axial direction against the force applied by the spring 323c, and thereby, the valve mechanism 323 opens the insertion mouth 31. On the other hand, if the insertion portion 51 is inserted into the insertion mouth 31 and the opening protrusion 322a inserted into the passage 53 presses the valve body 541, then the valve body 541 moves in the axial direction against the force applied by the spring 542, and thereby, the valve mechanism 54 opens the passage 53.

Figure 8:
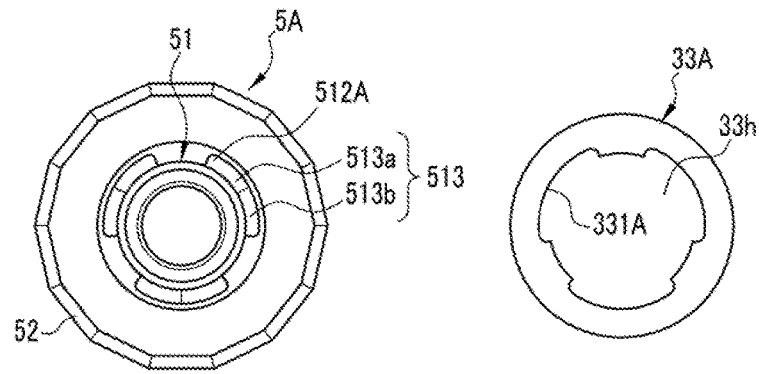
FIGS. 8(A) to 8(C) are each a plan view showing another example of the injection adapter and an identifying member of FIG. 1.
Figure 8:
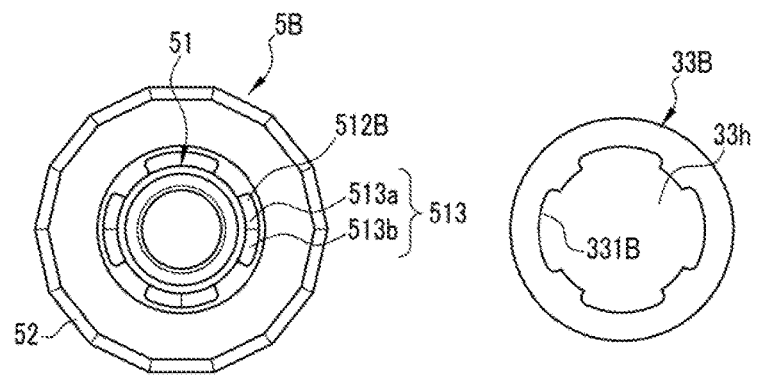
Figure 8:
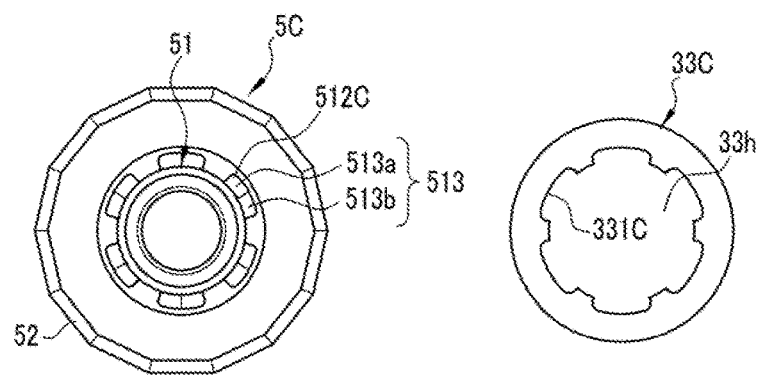

FIGS. 8(A) to 8(C) are plan views of injection adapters 5A to 5C and identifying members 33A to 33C respectively which correspond to volatile anesthetics other than sevoflurane. In FIG. 8(A), the injection adapter 5A and the identifying member 33A are formed with three keys 512A and three key groove 331A respectively which corresponds to, for example, isoflurane. In FIG. 8(B), the injection adapter 5B and the identifying member 33B are formed with four keys 512B and four key groove 331B respectively which corresponds to, for example, enflurane. Similarly, in FIG. 8(C), the injection adapter 5C and the identifying member 33C are formed with six keys 512C and six key groove 331C respectively which corresponds to, for example, halothane. The widths of the key 512 and the key groove 331 differ in accordance with the numbers of the keys 512 and the key groove 331 respectively. This enables the identifying member 33 to be quickly rotated by the inclined plane 513 if the insertion portion 51 is inserted into the insertion mouth 31. The widths of the key 512 and the key groove 331 become smaller as the numbers thereof become larger, and the widths become greater as the numbers become smaller. In summary, the injection adapter 5 and the identifying member 33 correspond to the volatile anesthetic 6 of a plurality of types in accordance with the numbers and widths of the keys 512 and the key groove 331.

Next, the operation will be described of the system 1 for preventing an erroneous anesthetic injection according to the above embodiment. When the volatile anesthetic 6 is injected into the anesthetic tank 2, the injection adapter 5 suitable for the anesthetic tank 2 is attached to the anesthetic container 4 storing the volatile anesthetic 6 suitable for the anesthetic tank 2. The base portion 52 of the injection adapter 5 and the collar 42 of the anesthetic container 4 are formed with the notch 52b and the protrusion 42a respectively which indicate the type of the volatile anesthetic 6 suitable for the anesthetic tank 2 by the widths and the arrangement intervals thereof. The injection adapter 5 is attached to the anesthetic container 4 by fitting the notch 52b onto the protrusion 42a, thereby preventing the injection adapter 5 from being attached to the unsuitable anesthetic container 4.

Figure 9:
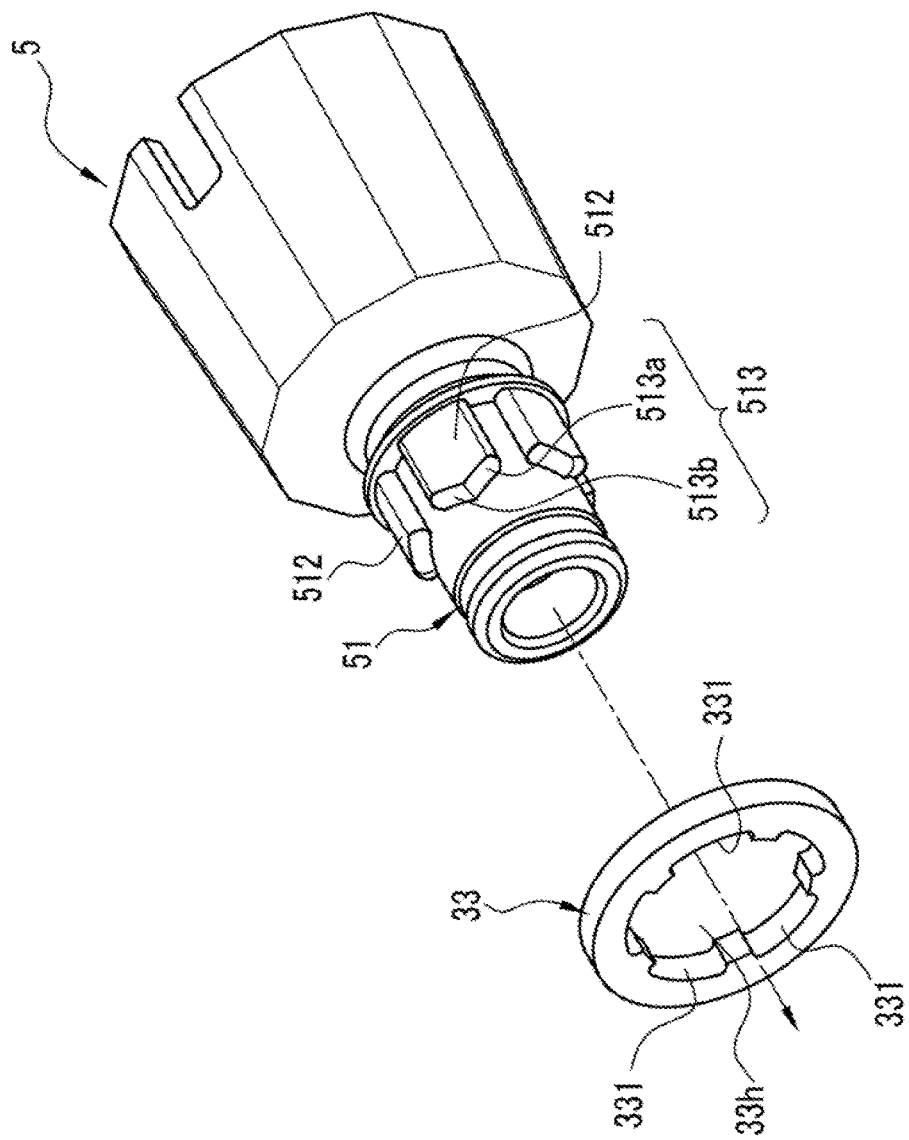
FIG. 9 is a perspective view showing a relation of the insertion of the insertion portion of the injection adapter into the identifying member of FIG. 1.

Subsequently, while holding the anesthetic container 4, the insertion portion 51 of the injection adapter 5 is inserted into the insertion mouth 31 of the erroneous-injection prevention portion 3. As shown in FIG. 9, the keys 512 formed in the peripheral surface of the insertion portion 51 come into contact with the identifying member 33 inside of the insertion mouth 31. Then, the keys (second identification portion) 512 press the key groove (first identification portion) 331 and thereby rotate the key groove 331 up to the position where the keys 512 engage with the key groove 331. Consequently, the insertion portion 51 of the injection adapter 5 is accepted into the key groove 331. In other words, the inclined planes 513 of the keys 512 press the key groove 331 and thereby rotate the identifying member 33 in the clockwise or counterclockwise direction.

If the shape of the key groove 331 is fit for the shape of the keys 512 of the insertion portion 51, then the identifying member 33 accepts the insertion portion 51 into the insertion mouth 31. As a result, the valve mechanism 323 of the insertion mouth 31 and the valve mechanism 54 of the insertion portion 51 are opened, and thereby, the volatile anesthetic 6 stored in the anesthetic container 4 flows through the erroneous-injection prevention portion 3 into the storage portion 21.

In contrast, if the shape of the key groove 331 is unfit for the shape of the keys 512 of the insertion portion 51, then the identifying member 33 accepts the insertion portion 51 into the insertion mouth 31. Therefore, the volatile anesthetic 6 unsuitable for the anesthetic tank 2 is hindered from being injected, so that the volatile anesthetics 6 of different types can be prevented from mixing together.

As described above, in the system 1 for preventing an erroneous anesthetic injection according to this embodiment, the insertion portion 51 of the injection adapter 5 is inserted into the insertion mouth 31 of the erroneous-injection prevention portion 3, and thereby, the inclined planes 513 of the keys 512 of the insertion portion 51 rotate the identifying member 33. Therefore, without rotating the anesthetic container 4, the insertion portion 51 can be inserted deep into the insertion mouth 31. This avoids loosening the attachment of the injection adapter 5 and thereby prevents a leak of the volatile anesthetic 6. Besides, the injection adapter 5 can be inserted into the insertion mouth 31 without positioning the keys 512 of the insertion portion 51 and the key groove 331 of the insertion mouth 31 so that the keys 512 engages with the key groove 331. Therefore, the injection work of the volatile anesthetic 6 becomes simpler.

In addition, the identifying member 33 is arranged on the outside of the insertion mouth 31, and hence, the volatile anesthetic 6 does not leak from the identifying member 33. This dispenses with: seal parts such as an O-ring; highly-precise machining necessary for preventing a leak of the volatile anesthetic 6; and the like. Furthermore, the identifying member 33 is arranged on the outside of the insertion mouth 31 and is only pressed by the cover member 324, so that the identifying member 33 can be easily exchanged. Therefore, even if the anesthetic tank 2 of a plurality of types is employed in accordance with the type of the volatile anesthetic 6, then the anesthetic tank 2 of each type can be utilized simply by exchanging the identifying member 33 alone. This makes it possible to produce the anesthetic tank 2 of the plurality of types at an extremely-low cost and with ease.

Furthermore, the key 512 of the insertion portion 51 is formed with the first inclined plane 513a for rotating the identifying member 33 in the counterclockwise direction (first direction) and the second inclined plane 513b for rotating the identifying member 33 in the clockwise direction (second direction). Therefore, the required rotational angle of the identifying member 33 narrows as compared with the case where the identifying member 33 is rotated along an inclined plane in only one direction. The narrower-angle rotation of the identifying member 33 enables the keys 512 and the key groove 331 to be positioned in a short period of time so that the keys 512 engage with the key groove 331. Therefore, the injection work of the volatile anesthetic 6 becomes quicker.

Moreover, the plurality of keys 512 and the plurality of key groove 331 are arranged at regular intervals around the center axis of the insertion portion 51 or the insertion mouth 31 respectively. Therefore, even if the keys 512 of the injection adapter 5 are inserted at any position into the insertion mouth 31, the identifying member 33 performs the positioning quickly.

Second Embodiment

Next, a second embodiment of the present invention will be described. The component elements of this embodiment which are identical with those of the first embodiment are given the same reference characters and numerals, and hence, their detailed description is omitted. FIG. 10 shows an injection adapter 5D and an identifying member 33D which have a plurality of key groove 514D formed in the insertion portion 51 and a plurality of keys 332D respectively. The key groove 514D and the keys 332D are the reverse arrangement of the keys 512 and the key groove 331 of the first embodiment. The keys 332D of the identifying member 33D each include an inclined plane 333 formed by a first inclined plane 333a and a second inclined plane 333b. Even if such keys and key groove are formed in the mutually reverse members, the same operation and advantages as the first embodiment can be obtained.

According to this embodiment, a choice can be optionally made as to which of the two members should be formed with a set of keys or a set of key groove in accordance with various conditions such as the shapes of the insertion portion 51 and the insertion mouth 31. This heightens the degree of freedom in design for the injection adapter 5 and the identifying member 33, thereby facilitating the injection work in the system 1 for preventing an erroneous anesthetic injection.

Figure 11:
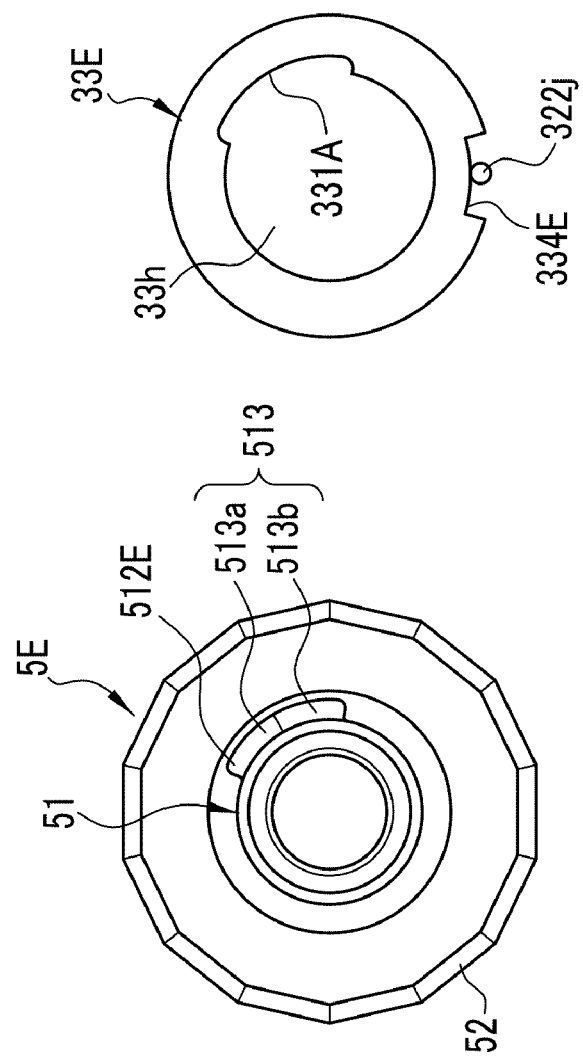
FIG. 11 is a plan view of an injection adapter and an identifying member each formed with a key and a key groove respectively.

In the above first and second embodiments, the plurality of keys and key groove are arranged at regular intervals in the circumferential directions. On the other hand, FIG. 11 shows an injection adapter 5E and an identifying member 33E which are formed with a single key 512E and a single key groove 331E respectively. The type of the volatile anesthetic 6 may be identified by the widths of the key 512E and the key groove 331E. In this case, in order to facilitate the positioning of the key 512E and the key groove 331E for fitting the key 512E into the key groove 331E, for example, it is preferable to form a notch 334E in the peripheral edge of the identifying member 33E, insert a restraint pin 322j provided in the end surface of the intermediate member 322 into the notch 334E and restrain the rotational range of the identifying member 33E.

Third Embodiment

Figure 12:
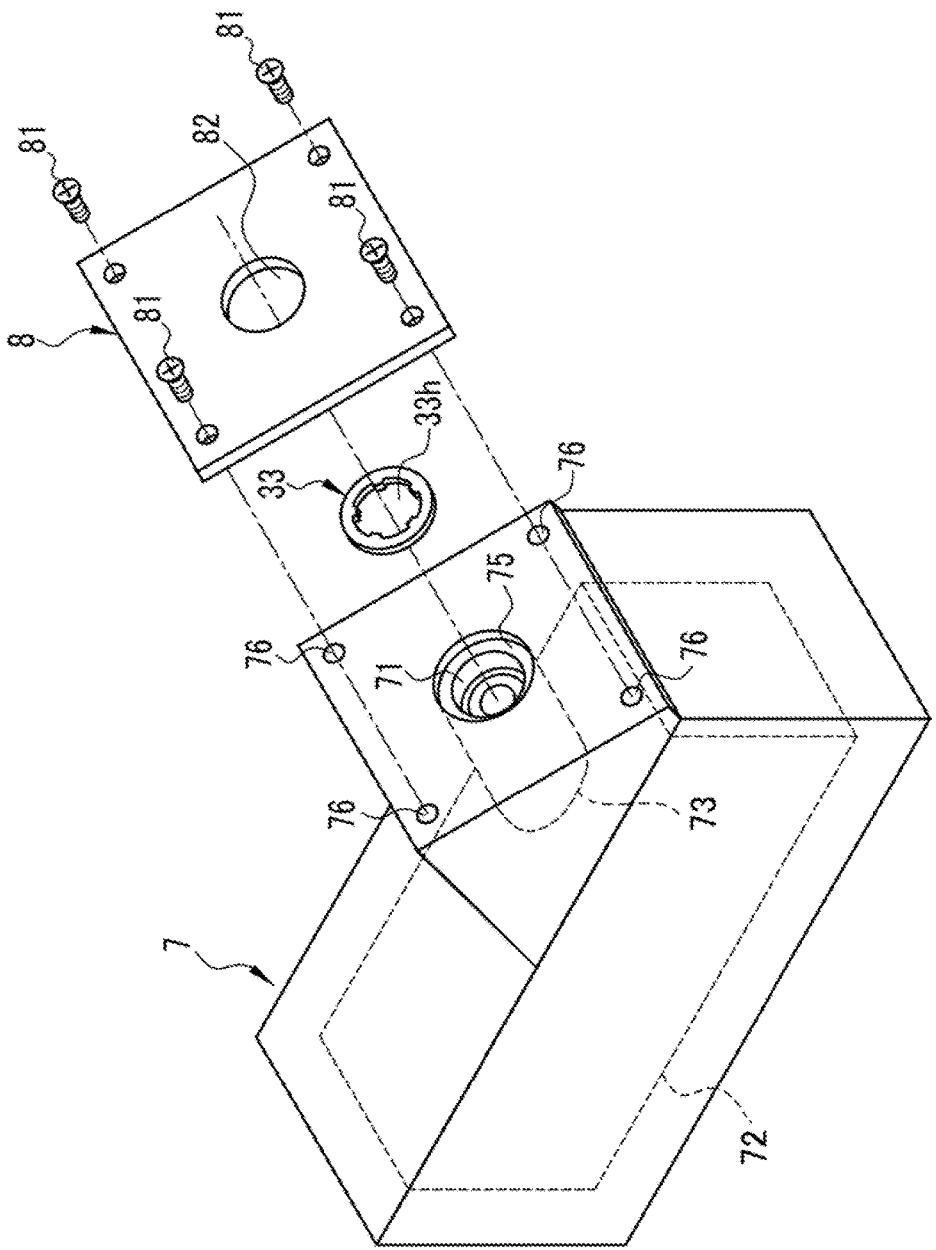
FIG. 12 is a perspective view showing the configuration of an anesthetic tank according to a third embodiment of the present invention.

FIG. 12 shows the configuration of an anesthetic tank 7 according to a third embodiment of the present invention. The anesthetic tank 7 includes an insertion mouth 71 for injecting a volatile anesthetic, and a storage portion 72 storing the volatile anesthetic injected from the insertion mouth 71. The anesthetic tank 7 differs from that of the first embodiment, for example, in that the anesthetic tank 7 is connected via piping and the like to an anesthetic vaporizer. The component elements of this embodiment which are identical with those of the first embodiment are given the same reference characters and numerals, and hence, their description is omitted.

The anesthetic tank 7 has a communicating passage 73 arranged between the insertion mouth 71 and the storage portion 72 so that both communicate with each other. The communicating passage 73 houses the component elements other than the identifying member 33 and the cover member 324 of the erroneous-injection prevention portion 3 of the first embodiment.

The anesthetic tank 7 is provided with an injection panel portion 74 which rises obliquely from the upper surface of the anesthetic tank 7. In the injection panel portion 74, the insertion mouth 71 is arranged so as to be obliquely above directed. The injection panel portion 74 is formed with a circular concave portion 75 for arranging the identifying member 33 on the periphery of the insertion mouth 71. The concave portion 75 has a depth slightly greater than the thickness of the identifying member 33 so that the identifying member 33 can rotate without any resistance and cannot be clatteringly shaken.

To the upper surface of the injection panel portion 74, a cover member 8 having the shape of a rectangular plate is attached, for example, by four screws 81 penetrating through the four corners. The injection panel portion 74 is formed with screw holes 76 for driving in the screws 81. The cover member 8 has an opening 82 formed in the position facing the insertion mouth 71 and the insertion hole 33h of the identifying member 33, and the insertion portion 51 of the injection adapter 5 can be inserted into the opening 82. The cover member 8 presses the peripheral part of the identifying member 33 from above, thereby preventing the identifying member 33 from slipping off.

In the anesthetic tank 7, the insertion portion 51 of the injection adapter 5 is inserted from the opening 82 of the cover member 8 through the insertion hole 33h into the insertion mouth 71. Therefore, the key groove 331 of the identifying member 33 collaborate with the keys 512 of the insertion portion 51, thereby preventing an erroneous injection of the volatile anesthetic.

As described above, the anesthetic tank 7 according to this embodiment is also capable of injecting the volatile anesthetic without loosening the attachment of the injection adapter 5. Moreover, the positioning of the injection adapter 5 at the time of the insertion is dispensable, thereby simplifying the injection work. In addition, the identifying member 33 is arranged on the outside of the insertion mouth 71, and hence, a volatile anesthetic does not leak from the identifying member 33. This dispenses with: seal parts such as an O-ring; highly-precise machining necessary for preventing a leak of the volatile anesthetic; and the like. Furthermore, the identifying member 33 is arranged on the outside of the insertion mouth 71 and is only pressed by the cover member 8, so that the identifying member 33 can be easily exchanged. Therefore, even if the anesthetic tanks 7 of a plurality of types are employed in accordance with the types of volatile anesthetics, then the individual anesthetic tanks 7 can be utilized simply by exchanging the identifying members 33 alone. This makes it possible to produce the plurality of types of anesthetic tanks 7 at an extremely-low cost and with ease.

Although the embodiments of the present invention have been above described, the present invention is not limited to the embodiments as specific configurations thereof. Without departing from the scope of the present invention, variations or the like in design should be included in the present invention. For example, the present invention can also be applied to the systems for preventing an erroneous anesthetic injection which have the configurations of Patent Documents 1 to 3. Besides, in the individual embodiments described above, the keys are formed with the inclined planes, but both the keys and the key groove may be formed with inclined planes respectively. According to this configuration, an identifying member formed therewith is rotated by leading the inclined planes on the one hand to come into contact with the inclined planes on the other hand. Hence, the inclined planes on the one hand slide on the inclined planes on the other hand, so that the identifying member can be more smoothly rotated.

DESCRIPTION OF THE SYMBOLS 1 system for preventing an erroneous anesthetic injection
2 anesthetic tank
21 storage portion
3 erroneous-injection prevention portion
31 insertion mouth
33 identifying member
331 key groove (first identification portion)
4 anesthetic container
5 injection adapter
51 insertion portion
6 volatile anesthetic
51 insertion portion
512 key (second identification portion)
513 inclined plane
7 anesthetic tank
71 insertion mouth
72 storage portion
8 cover member

The invention claimed is:

1. An anesthetic tank which includes an insertion mouth for inserting an injection adapter attached to a mouth portion of an anesthetic container and a storage portion communicating with the insertion mouth, the storage portion being injected from the injection adapter inserted into the insertion mouth with a volatile anesthetic inside of the anesthetic container, comprising:

an identifying member which: has a disk shape; is arranged on the outside of the insertion mouth and rotatable around the center axis of the insertion mouth; has an insertion hole formed in the position facing the insertion mouth, the insertion hole being used for inserting the injection adapter; and has a first identification portion formed in the internal surface of the insertion hole, the first identification portion being used for identifying the type of the volatile anesthetic to be injected in collaboration with a second identification portion formed in the injection adapter; and a cover member which has an opening formed in the position facing the insertion mouth and the insertion hole, the opening being used for inserting the injection adapter, and presses the peripheral part of the identifying member from above the identifying member, the identifying member accepting the injection adapter by rotating up to the position where the first identification portion engages with the second identification portion if the injection adapter having the second identification portion fit for the first identification portion is inserted into the insertion hole and thereby the second identification portion presses the first identification portion, and hindering insertion of the injection adapter by leading the first identification portion to block the space necessary for the insertion of the second identification portion if the injection adapter having the second identification portion unfit for the first identification portion is inserted into the insertion hole.

2. The anesthetic tank according to claim 1, wherein as the anesthetic tank, a plurality of types are employed in accordance with types of the volatile anesthetic, and the plurality of types of anesthetic tanks are mutually different only in the identifying member.

3. The anesthetic tank according to claim 1, wherein the anesthetic tank; is of a plurality of types in accordance with types of the volatile anesthetic, and each type of the anesthetic tank differs only in the identifying member.

4. A system for preventing an erroneous anesthetic injection which includes an injection adapter attached to a mouth portion of an anesthetic container and the anesthetic tank according to claim 1,
   wherein the injection adapter includes the second identification portion formed in the peripheral surface of an insertion portion of the injection adapter inserted into the insertion mouth, the second identification portion being used for identifying the type of the volatile anesthetic to be injected into the anesthetic tank in collaboration with the first identification portion.

5. A system for preventing an erroneous anesthetic injection which includes an injection adapter attached to a mouth portion of an anesthetic container and the anesthetic tank according to claim 2,
   wherein the injection adapter includes the second identification portion formed in the peripheral surface of an insertion portion of the injection adapter inserted into the insertion mouth, the second identification portion being used for identifying the type of the volatile anesthetic to be injected into the anesthetic tank in collaboration with the first identification portion.

6. The system for preventing an erroneous anesthetic injection according to claim 4, wherein either the first identification portion or the second identification portion is a set of keys which indicates the type of the volatile anesthetic by at least any one of the widths, the positions and the number of the keys, and the other is a set of key groove which is fit for the set of keys.

7. The system for preventing an erroneous anesthetic injection according to claim 6, wherein each of the keys is formed with a first inclined plane for rotating the identifying member in a first direction around the center axis of the insertion mouth and a second inclined plane for rotating the identifying member in a second direction opposite to the first direction.

8. The system for preventing an erroneous anesthetic injection according to claim 6, wherein a plurality of the keys and a plurality of the key groove are arranged at regular intervals around the center axis of the insertion portion or the insertion mouth respectively.

9. The system for preventing an erroneous anesthetic injection according to claim 7, wherein a plurality of the keys and a plurality of the key groove are arranged at regular intervals around the center axis of the insertion portion or the insertion mouth respectively.

* * * * *